United States Patent [19]

Nathanson et al.

[11] Patent Number: 4,681,763
[45] Date of Patent: Jul. 21, 1987

[54] COMPOSITION FOR STIMULATING BONE GROWTH

[75] Inventors: Mark A. Nathanson, Philadelphia, Pa.; A. H. Reddi, Kensington, Md.; T. K. Sampath, Arlington, Mass.

[73] Assignee: University of Medicine and Dentistry of New Jersey, Newark, N.J.

[21] Appl. No.: 743,598

[22] Filed: Jun. 11, 1985

[51] Int. Cl.$^4$ ............................................. A61K 35/12
[52] U.S. Cl. ..................................................... 424/95
[58] Field of Search .......................................... 424/95

[56] References Cited

U.S. PATENT DOCUMENTS 4,440,750  4/1984  Glowacki et al. ..................... 424/95
4,563,350  1/1986  Nathan et al. ......................... 424/95

FOREIGN PATENT DOCUMENTS 0048111  3/1979  U.S.S.R. ................................ 424/95

OTHER PUBLICATIONS

Chem Abst. 102: 22167m, 1985.
Chem Abst. 103: 128679v, 1985.
Proc. Natl. Acad. Sci. USA, 81: 3419-3423, Jun., 1984.
Proc. Natl. Acad. Sci. USA, 82: 2267-2271, Apr. 1985.
Proc. Natl. Acad. Sci. USA, 81: 371-375, Jan. 1984.

Primary Examiner—Johnnie R. Brown
Assistant Examiner—John W. Rollins
Attorney, Agent, or Firm—Popper, Bobis & Jackson

[57] ABSTRACT

There is disclosed a method of recovering a material active in the formation of new bone and cartilage from demineralized bone extract and the composition of said material on a pliable physiologically acceptable support.

12 Claims, No Drawings

COMPOSITION FOR STIMULATING BONE GROWTH

This invention was made with Government support under Grant R01-AM28240 awarded by the National Institutes of Health. The Government has certain rights in this invention.

This invention relates to a method of recovering a solid material capable of stimulating new bone growth and the composition of said material on a pliable physiologically acceptable support which is capable of implanation into animals to induce new bone growth.

The post-surgical healing of bone trauma, defects and fractures is frequently hindered in elderly patients, diabetics and other known patient groups. Prior investigators have reported the formation of new bone in vivo after the implantation of demineralized bone into the muscle tissue of test subjects. Muscle tissue normally will not form bone in the absence of demineralized bone; similarly the presence of undemineralized bone does not stimulate host muscle tissue to form new bone. Clinical use of demineralized bone has induced allergic reactions to the cellular components contained therein, and therefore has received little attention.

The type of bone produced in vivo is endochondral bone, which refers to the secondary formation of bone as a growth upon a prior-occuring cartilage model. Thus, in vivo cartilage is the first product and it is then replaced by bone.

In the in vitro test system, demineralized bone in the presence of muscle tissue induces the production of cartilage only, whereas such muscle tissue fails to produce cartilage in the absence of demineralized bone. Formation of cartilage in vitro occurs in an identical fashion to cartilage formed in vivo and does not yield bone. The lack of bone formation is due to the lack of a host organism's vascular system, as bone cells are currently thought to arise from vascular-derived cells. In all other respects the in vitro and in vivo systems are regarded as equivalent.

In accordance with one aspect of the present invention, there is provided a solid material capable of stimulating formation of new bone in vivo and cartilage in vitro which is derived from an extract of demineralized bone.

In accordance with a second aspect of the present invention, there is provided a method of depositing onto a physiologically acceptable support a solid material which is derived from an extract of demineralized bone.

These and other objects of the present invention are achieved by recovering a solid material capable of stimulating new bone growth from an extract of demineralized bone which is then combined with a pliable physiologically acceptable support. This composition may then be implanted in an animal to induce new bone growth. The preferred support for this purpose is a physiologically acceptable collagen support.

More particularly, the material capable of stimulating formation of new bone in vivo is derived from demineralized bone by use of an extraction solvent capable of extracting this material therefrom. The active component contained in the extraction solvent is then deposited on a physiologically acceptable support in a novel manner so as to provide a novel composition comprised of such material supported on a pliable physiologically acceptable support. The resulting composition may be dried for storage, and rehydrated at a later time for implantation.

The support is one which is capable of accepting the material in solid form and which is physiologically acceptable in that it may be implanted in vivo without rejection. The preferred support for this purpose is a physiologically acceptable pliable collagen support. Physiologically acceptable pliable collagen supports are generally known in the art; it is to be understood that other materials which are conventionally employed as surgical implants may also be used. As representative examples of such materials, there may be mentioned commercially available resorbable polymers such as synthetic foams and fabrics.

Although applicant is not presently capable of providing the chemical characteristics of the material which is derived from demineralized bone, it is known that such material is characterized as being soluble in aqueous guanidine hydrochloride. As a result, aqueous hydrochloride is preferably employed as the extraction solvent. It is to be understood, however, that although the material is characterized as being soluble in guanidine hydrochloride, it is possible to employ other compounds for extracting the material from demineralized bone. For example, it is known that urea is suitable for extracting such material from demineralized bone; as a result, the scope of the invention is not limited to the use of guanidine as an extraction solvent.

After obtaining the extract of demineralized bone in an extraction solvent, the extract is applied to the pliable support. The material is caused to be deposited from the extract onto the support in solid form by adding a second compound within which the extraction solvent is soluble so as to provide a solution in which the material is insoluble, whereby such material precipitates onto the solid support. The extraction solvent is then washed away by repeated application of the second compound. The second compound is volatile and is then removed by standard laboratory drying procedures. In this manner, material is deposited in solid form on the physiologically acceptable support for subsequent use in an implantation in the absence of extraction solvent or other compounds and in a sterile state.

In accordance with a preferred aspect of the present invention, ethanol is employed as the compound for precipitating the material from the extraction solvent onto the support and which sterilizes the resultant composition. Moreover, since the preferred extraction solvent, guanidine, is soluble in ethanol, ethanol also functions to effectively wash away and remove the guanidine from the support. As a result, the precipitate of material in solid form is deposited onto the support in the essential absence of extraction solvent.

Although ethanol is the preferred agent for precipitating the material onto the solid support, it is to be understood that other compounds and in particular alcohols, e.g. isopropanol, may be employed to precipitate the material from the solution applied to a solid support. The precipitating agent and in particular ethanol is employed in an amount, concentration and for a time to effectively deposit the material in solid form onto the support.

The extraction of the material from demineralized bone is generally known in the art; accordingly no further details in this respect are required by those skilled in the art. The selection of optimal materials and conditions should be apparent to those skilled in the art from the teachings herein.

The present invention is further described with respect to the following examples; however, the scope of the invention is not to be limited thereby;

EXAMPLE I

Preparation of Guanidine Hydrochloride Extracts of Demineralized Bone

Demineralized bone is prepared as described by Nathanson in Dev. Bio., Vol. 64:99-117, and extracellular matrix components are extracted with 6.0 M guanidine hydrochloride in 50 mM Tris buffer, pH 7.0 (10 segments per 100 ml), at 40° for 72 hr with constant stirring, in the presence of protease inhibitors. The insoluble demineralized bone residue is washed three times with distilled water and lyophilized. The insoluble residue is referred to as "inactivated" bone in recognition of its lack of activity in stimulating formation of cartilage in vitro and bone in vivo by virtue of the extraction of its activity by guanidine hydrochloride. The inactivated residue is used as an additional control substratum in in vivo and in vitro testing (see also Examples II and III.) It is understood that several means of preparing extracts are known to those skilled in the art. Accordingly an extract may also be prepared from pulverized bone by extraction as above in 4.0M guanidine hydrochloride.

A usuable extract prepared by the methods described herein is used in concentrations of from 5 to 20 mg. protein/ml. Twenty microliters of the resulting guanidine extract, equivalent to from 100 to 400 micrograms of demineralized bone extract, is added to the surface of a test substratum which is collagen gel. The collagen gel is prepared as in Example 2.

The resulting composition is dried under sterile air for one (1) hour. This process is repeated from one (1) to three (3) times to attain a higher level of extract on the surface of the support.

The composition is then washed with 0.5 ml of 85% ethanol, which is maintained at $-10°$ C., and the excess liquid is drained. The washing step is repeated five (5) times, after which the composition is bathed in 85% ethanol at $-10°$ C. for 30 minutes to remove the guanidine and effectively dehydrate the composition without denaturing the extract.

The composition is lyophilized using a standard freeze drying apparatus.

Prior to implantation the composition is rehydrated by soaking in normal saline. The composition is then used by conventional technology to induce formation of new bone and new cartilage in vivo. Unextracted demineralized bone and inactivated bone reconstituted with the extract as described above are equivalent in their potential to form new bone and new cartilage.

EXAMPLE II

Preparation of Collagen Gel

Type I collagen is extracted from the tail tendons of adults rats in 0.5M acetic acid and prepared for use in vitro by standard laboratory technology. Collagen gels are cast on millipore filters, also by standard laboratory methodology (pore size 0.45 um; type HA; Millipore), and sterilized prior to use by immersion in 70% ethanol for 1 hr. Two applications are sufficient to provide a gel that when rehydrated is peeled intact from the filter.

EXAMPLE III

Tissue Preparation and Cultivation For In Vitro Testing

It is understood that testing in vitro is done to confirm activity of guanidine extracts of demineralized bone. Skeletal muscle is used as the test tissue and is excised from the thighs of 19 to 20 day fetal rats. Thigh muscle is asceptically isolated into an aliquot of ice-cold complete culture medium. During the isolation procedure, contaminant dermal, vascular, and nervous tissue are mechanically removed. Cultures consist of aliquots of cleaned skeletal muscle grown on (1) a substratum of 3 to 5 mm hemicylindrical segments of demineralized diaphyseal bone; (2) gels of type I collagen (reconstituted with an extract of demineralized bone as described above), (3) unreconstituted gels of type I collagen, and (4) inactivated residue of demineralized bone. For each of the experiments described below, at least three parallel cultures are prepared and each experiment is performed twice to assure uniformity.

Complete culture medium consisting of medium CMRL-1066 containing 15% fetal calf serum (pretested and heat-inactivated), 0.225% sodium bicarbonate, and gentamycin at 50 ug/ml is utilized. CMRL-1066 is added as a 10x concentrate, such that the final medium contains a 1x nutrient base. Explants onto demineralized bone and collagen gels are fed on alternate days by changing one-half to three-fourths of the culture medium. Cultures are maintained at 30° C. in a water-jacketed incubator (National Appliance, Portland, OR) in an atmosphere of 5% CO/95% air. The culture period for the present experiment is set at 18 days, to provide sufficient time for chondrogenesis to occur.

Reconstitution

The guanidine-HCl extract of pulverized demineralized bone (particle size, 74–420 um) is used via the method described herein to reconstitute inactivated bone residue and collagen gels (samples 1 and 4 above). Reconstitution was accomplished by alcohol precipitation as follows: segments of inactivated bone and collagen gels are placed in a sterile glass Petri dish. To the surface of each is added 20 microliters of a guanidine hydrochloride extract of bone matrix containing various concentrations of total protein (usually 0.5–2 mg of protein/100 ul.) The reconstituted segments and collagen gels are air dried in a laminar flow hood for 1 hr. Coating is repeated once more with the same concentration of extract, and protein is precipitated onto the bone segments of collagen gels by washing with 0.5 ml of cold 85% ethanol. Petri dishes are cooled to $-10°$ C. before and during alcohol precipitation. The guanidine hydrochloride ethanol supernatant is then removed from the dishes and the entire procedure is repeated five times. Reconstituted bone segments and collagen gels are placed in cold 85% ethanol for 30 min. and lyophilized.

Histology (used for both in vivo and in vitro testing)

Samples grown in vitro are fixed for histological examination in 10% formalin in neutral phosphate buffer and embedded in Paraplast Plus. Seven-micrometer serial sections were stained with toluidine blue. In vivo samples are fixed in Bouin's fluid and embedded in JB4 plastic medium (Polysciences, Warrington, PA).

One-micrometer sections are then stained with toluidine blue.

Cartilage Differentiation in vitro

When demineralized bone is used as a control, cartilage is observed histologically in 100% of the cases. When gels of type I collagen that are not reconstituted are used as a control, regeneration of muscle is observed. The chondrogenic response occurs when a similar collagen gel is reconstituted with an extract of demineralized bone. Cartilage has been detected in each of the reconstituted collagen gels tested thus far. The reconstituted gels contain nodules of hyaline cartilage. Finally, the inactive residue of demineralized bone supports poor cellular growth, poor muscle regeneration, and no cartilage formation.

EXAMPLE IV

Biochemical Confirmation of Chondrogenesis in vitro

Extraction and fractionation of proteoglycans

Explants grown on reconstituted demineralized bone and collagen gels are labeled with $Na_2{}^{35}SO_4$ and minced with a scalpel prior to dissociative extraction in 4.0M guanidine-HCl in 0.05M sodium acetate buffer (pH 5.8) in the presence of protease inhibitors. Salts and unincorporated isotopes are removed by dialysis in the presence of protease inhibitors. After dialysis, an aliquot of the clear extract is assayed for radioactivity and the remainder is frozen at $-80°$ C. and lyophilized. Residual bone matrix and collagen fragments are digested with a quaternary amine solvent, Solusol (National Diagnostics, Somerville, NJ), and the radioactivity is determined in a specially designed counting solution, Soluscint-0 (National Diagnostics, Somerville, NJ) to measure the amount of unextractable isotope.

Proteoglycans are fractionated by molecular sieve chromatography on columns of Sepharose CL-2B under associative conditions. Lyophilized proteoglycans are dissolved in 0.5 ml of the dissociative solvent, lacking benzamidine. Proteoglycans are then permitted to reassociate during dialysis against an associative buffer consisting of 0.5M ammonium acetate in 20% ethanol. Dialysis is carried out at 4° C. against 2 liters of associative buffer for 4 hr. followed by a second 2 liters overnight. Five microliters of aqueous phenol red and 100 ug of carrier proteoglycan monomer from rat chondrosarcoma are added to the dialyzed extracts, which are then clarified by centrifugation at 20,000x g and 4° C. for 15 min. Following sample application, the analytical columns are eluted at 40° C. at a constant pressure of 30 cm.

The elution patterns of proteoglycan extracts from samples of skeletal muscle grown on reconstituted demineralized bone, and collagen gels reconstituted with an extract of demineralized bone, were similar to those of authentic rat cartilage. In particular, high molecular weight proteoglycans were clearly present and these proteoglycans are diagnostic for cartilage. This final example demonstrates that in addition to the reproducable histologic appearance of bone in vivo and cartilage in vitro, the reconstituted extract promotes full biochemical differentiation of cartilage in vitro.

The present invention is particularly advantageous in that the extract of demineralized bone is provided in a solid form, and is capable of being easily implanted into an animal, and in particular humans. The use of a pliable physiologically acceptable support, in combination with solidified extract, enables such implantation to be easily performed. Other advantages of the invention described herein as well as numerous modifications and variations of the above described invention are possible and will become obvious to those skilled in the art in light of the above teachings, and accordingly are within the scope of the appended claims.

What is claimed is:

1. A composition for implantation into animals to stimulate new bone growth comprising:
    a material capable of stimulating formation of new bone and cartilage in vivo derived from demineralized bone by use of aqueous guanidine hydrochloride, said material deposited by precipitation onto a pliable physiologically acceptable support.

2. The composition of claim 1, wherein the pliable physiologically acceptable support comprises collagen gel.

3. A method of recovering a material capable of stimulating cartilage in vivo derived from demineralized bone by use of aqueous guanidine hdrochloride comprising:
    (a) applying a solution of said material in aqueous guanidine hydrochloride to a pliable physiologically acceptable support;
    (b) precipitating said material from the solution of aqueous guanidine hydrochloride onto the support by the addition of a precipitating agent; and
    (c) removing the volatile alcohol solvent.

4. The method of claim 3, wherein the precipitating agent is a volatile alcohol solvent.

5. The method of claim 3, wherein the temperature of the precipitating agent is $-10°$ C.

6. The method of claim 3, wherein the concentration of the precipitating agent is 85%.

7. A method of preparing an implant to induce new bone growth which comprises
    (a) providing a solution of a material capable of stimulating formation of new bone and cartilage in vivo derived from demineralized bone by use of aqueous guanidine hydrochloride;
    (b) applying said solution to a pliable physiologically acceptable support; and
    (c) percipitating said material from said solution onto said support.

8. The method of claim 7 wherein the pliable physiologically acceptable support is a collagen gel.

9. The method of claim 7 wherein the precipitation of said material is caused by the addition of an alcohol solvent.

10. The method of claim 9 wherein the alcohol solvent is ethanol or isopropanol.

11. A method of stimulating formation of new bone and cartilage in vivo which comprises implanting in a patient in need of such stimulation therapy an implant which comprises a material capable of stimulating formation of new bone and cartilage in vivo derived from demineralized bone by use of aqueous guanidine hydrochloride said material deposited by precipitation onto a pliable physiologically acceptable support.

12. The method of claim 11 wherein the physiologically acceptable support is a collagen gel.

* * * * *